United States Patent [19]

Su et al.

[11] Patent Number: 5,082,917
[45] Date of Patent: Jan. 21, 1992

[54] PIPERAZINE DERIVATIVES AS CHAIN EXTENDERS IN POLYUREA ELASTOMER SYSTEMS AND METHOD MAKING SAME

[75] Inventors: Wei-Yang Su, Austin; Dudley J. Primeaux, II, Elgin; Donald H. Champion, Pflugerville, all of Tex.

[73] Assignee: Texaco Chemical Co., White Plains, N.Y.

[21] Appl. No.: 529,839

[22] Filed: May 29, 1990

[51] Int. Cl.$^5$ .................... C08G 18/32; C08G 18/16; C08G 18/14
[52] U.S. Cl. ......................... 528/68; 528/60; 528/76; 528/77; 521/51; 521/159; 521/160; 521/163; 521/167
[58] Field of Search .................. 528/73, 76, 77, 78, 528/44, 60, 68, 76, 77; 521/176, 51, 163, 167, 159, 160

[56] References Cited

U.S. PATENT DOCUMENTS

| | | | |
|---|---|---|---|
| 4,433,067 | 2/1984 | Rice et al. | 521/51 |
| 4,474,901 | 10/1984 | Dominguer | 521/163 |
| 4,530,941 | 7/1985 | Turner et al. | 528/73 |
| 4,689,356 | 8/1987 | Peffley et al. | 521/159 |
| 4,801,674 | 1/1989 | Scott, Jr. et al. | 528/68 |
| 4,806,615 | 2/1989 | Rice et al. | 528/68 |
| 4,902,768 | 2/1990 | Gerkin et al. | 528/68 |

Primary Examiner—John Kight, III
Assistant Examiner—Duc Truong
Attorney, Agent, or Firm—Robert A. Kulason; James J. O'Loughlin; Dominick G. Vicari

[57] ABSTRACT

A polyurea elastomer is disclosed. The elastomer includes an isocyanate, an amine terminated polyoxyalkylene polyol, and a chain extender. The isocyanate is preferably a quasi-prepolymer of an isocyanate and a material selected from at least one polyol, a high molecular weight polyoxyalkyleneamine or a combination thereof. The chain extender includes a minor amount of a tetraalkylpiperazine and a major amount of diethyltoluenediamine. A one-step method of making the tetraalkylpiperazine and tetraalkylpiperazinone is also disclosed. The method includes reacting a 2-amino-2-alkyl-1-alkanol in the presence of a nickel-iron-copper-manganese catalyst.

26 Claims, No Drawings

PIPERAZINE DERIVATIVES AS CHAIN EXTENDERS IN POLYUREA ELASTOMER SYSTEMS AND METHOD MAKING SAME

BACKGROUND OF THE INVENTION

1. Field of the Invention

The present invention relates generally to polyurea elastomers and, more specifically, to spray and reaction injection molded polyurea elastomer systems which employ novel chain extenders. This invention also relates to a method of making a compound which is used as a component of the chain extenders.

2. Description of Background Art

Elastomer systems are commonly recognized as, among other things, coating materials, with spray polyurea elastomer systems being particularly useful when employed in this capacity. Spray polyurea elastomers are also employed in other open mold spraying applications for part production. Polyurea elastomers are also used for part production in closed mold applications, such as reaction injection molding (RIM) and reinforced reaction injection molding (RRIM). In addition, polyurea elastomers can be used in small mold filling type work, such as electric potting work.

Polyurea elastomer systems are generally prepared by reacting an isocyanate with an active hydrogen component in the presence of a chain extender. One of the most widely employed chain extenders is diethyltoluenediamine (DETDA), a product of Ethyl Corp. Polyurea elastomer systems fabricated from, among other things, DETDA, generally exhibit good processing characteristics. The chain extenders described herein are used in polyurea elastomer systems to replace a small percentage of DETDA, thereby providing an improvement in cure rate and tensile strength.

U.S. Pat. No. 3,979,364 describes the use of aminated polyethers as hereinafter used as a component with a polyol to make an elastomer.

U.S. Pat. No. 3,666,788 describes the use of cyanoalkylated aminated polyethers in spray systems.

U.S. Pat. Nos. 4,379,729; 4,444,910, and 4,433,067 describe elastomers which are prepared using a high molecular weight amine terminated polyether, an aromatic diamine chain extender and an aromatic polyisocyanate which may merely be a polyisocyanate or a quasi-prepolymer prepared from a polyol reacted with a polyisocyanate wherein some isocyanate groups are still left unreacted. Various patents have been applied for and received using the basic combination recited above, as well as various mold release agents and other additives, such as catalysts and fillers, including glass fibers; for example, see U.S. Pat. No. 4,607,090.

U.S. Pat. No. 3,714,128 describes cyanoalkylated polyoxyalkylene polyamines which are useful for slowing the gelling or hardening of the polyurea component so that good mixing of the isocyanate and amine components can be attained, which gives the sprayed material ample time to adhere and level before gelation of the polyurea coating occurs. This patent does not describe the particular chain extenders employed in the elastomer of the present invention.

U.S. Pat. No. 4,806,615 describes reaction injection molded elastomers consisting of a cured reaction product of primary or secondary amine terminated polyethers of greater than 1500 molecular weight, an aromatic polyisocyanate, a combination of an unsubstituted aromatic diamine chain extender, and a substituted acyclic aliphatic diamine chain extender.

U.S. Pat. No. 4,218,543 describes the use of high molecular weight polyols, certain aromatic diamines and isocyanates for the production of RIM parts. This patent specifically claims as a chain extender 1-methyl-3,5-diethyl-2,4-diaminobenzene (diethyltoluenediamine) and its isomer.

U S. Pat. No. 4,523,004 discloses a substituted aromatic diamine chain extender in a RIM product.

U.S. Pat. No. 4,631,298 discloses blending various slower reacting chain extenders with diethyltoluenediamine in a RIM system using amine terminated polyethers.

U.S. Pat. No. 4,585,850 describes a reaction injection molded elastomer made by reacting, in a closed mold, an amine terminated polyether of greater than 1500 average molecular weight, having greater than 50 percent of their active hydrogens in the form of amine hydrogens; a chain extender; flaked glass pretreated with an amino silane coupling agent; and an aromatic polyisocyanate.

Thus, it is our understanding that a polyurea elastomer system which incorporates the particular chain extenders described hereinbelow has heretofore been unavailable. It is our further understanding that the one-step method described herein for making the chain extenders has also been unavailable.

SUMMARY OF THE INVENTION

Accordingly, the present invention relates to a polyurea elastomer which comprises an (A) component and a (B) component. The (A) component includes an isocyanate. Preferably, the isocyanate of component (A) includes a quasi-prepolymer of an isocyanate and a material selected from at least one polyol, a high molecular weight polyoxyalkyleneamine or a combination of these materials. The (B) component includes (1) an amine terminated polyoxyalkylene polyol and (2) a chain extender which includes a minor amount of a tetraalkylpiperazine and a major amount of diethyltoluenediamine (DETDA).

Advantageously, when the chain extenders disclosed herein are used to prepare the polyurea elastomer of the present invention, the resulting elastomer exhibits an improved cure rate and tensile strength.

The present invention also relates to a one-step method of making tetraalkylpiperazines and tetraalkylpiperazinones. Specifically, the method comprises reacting, in one step, and under suitable reaction conditions, a 2-amino-2-alkyl-1-alkanol in the presence of a catalyst composition which includes nickel and at least one other transition metal, to produce said tetraalkylpiperazines and said tetraalkylpiperazinones. Preferably, the other transition metals include iron, copper and/or manganese.

DESCRIPTION OF THE PREFERRED EMBODIMENTS

The isocyanates employed in component (A) are those known to one skilled in the art. Thus, for instance, they can include aliphatic isocyanates of the type described in U.S. Pat. No. 4,748,192. Accordingly, they are typically aliphatic diisocyanates and, more particularly, are the trimerized or the biuretic form of an aliphatic diisocyanate, such as hexamethylene diisocyanate, or the bifunctional monomer of the tetraalkyl xylene diisocyanate, such as the tetramethyl xylene diisocyanate. Cyclohexane diisocyanate is also to be considered a preferred aliphatic isocyanate. Other useful aliphatic polyisocyanates are described in U.S. Pat. No. 4,705,814. They include aliphatic diisocyanates, for example, alkylene diisocyanates with 4 to 12 carbon atoms in the alkylene radical, such as 1,12-dodecane diisocyanate and 1,4-tetramethylene diisocyanate. Also described are cycloaliphatic diisocyanates, such as 1,3- and 1,4-cyclohexane diisocyanate, as well as any desired mixture of these isomers; 1-isocyanato-3,3,5-trimethyl-5-isocyanatomethyl-cyclohexane (isophorone diisocyanate); 4,4'-, 2,2'- and 2,4'-dicyclohexylmethane diisocyanate, as well as the corresponding isomer mixtures and the like.

A wide variety of aromatic polyisocyanates may be used to form the elastomer of the present invention. Typical aromatic polyisocyanates include p-phenylene diisocyanate, polymethylene polyphenylisocyanate, 2,6-toluene diisocyanate, dianisidine diisocyanate, bitolylene diisocyanate, naphthalene-1,4-diisocyanate, bis(4-isocyanatophenyl)methane, bis(3-methyl-3-isocyanatophenyl)methane, bis(3-methyl-4-isocyanatophenyl)methane, and 4,4'-diphenylpropane diisocyanate.

Other aromatic polyisocyanates used in the practice of the invention are methylene-bridged polyphenyl polyisocyanate mixtures which have a functionality of from about 2 to about 4. These latter isocyanate compounds are generally produced by the phosgenation of corresponding methylene bridged polyphenyl polyamines, which are conventionally produced by the reaction of formaldehyde and primary aromatic amines, such as aniline, in the presence of hydrochloric acid and/or other acidic catalysts. Known processes for preparing polyamines and corresponding methylene-bridged polyphenyl polyisocyanates therefrom are described in the literature and in many patents, for example, U.S. Pat. Nos. 2,683,730; 2,950,263; 3,012,008; 3,344,162; and 3,362,979.

Usually, methylene-bridged polyphenyl polyisocyanate mixtures contain about 20 to about 100 weight percent methylene diphenyldiisocyanate isomers, with the remainder being polymethylene polyphenyl diisocyanates having higher functionalities and higher molecular weights. Typical of these are polyphenyl polyisocyanate mixtures containing about 20 to 100 weight percent diphenyldiisocyanate isomers, of which 20 to about 95 weight percent thereof is the 4,4'-isomer with the remainder being polymethylene polyphenyl polyisocyanates of higher molecular weight and functionality that have an average functionality of from about 2.1 to about 3.5. These isocyanate mixtures are known, commercially available materials and can be prepared, for instance, by the process described in U.S. Pat. No. 3,362,979.

By far, the most preferred aromatic polyisocyanate is methylene bis(4-phenylisocyanate) or MDI. Pure MDI, quasi-prepolymers of MDI, modified pure MDI, etc., are useful. Materials of this type may be used to prepare suitable RIM elastomers. Since pure MDI is a solid and, thus, often inconvenient to use, liquid products based on MDI or methylene bis(4-phenylisocyanate) are used herein. U.S. Pat. No. 3,394,164 describes a liquid MDI product. More generally, uretonimine modified pure MDI is included also. This product is made by heating pure distilled MDI in the presence of a catalyst. The liquid product is a mixture of pure MDI and modified MDI and is represented as follows:

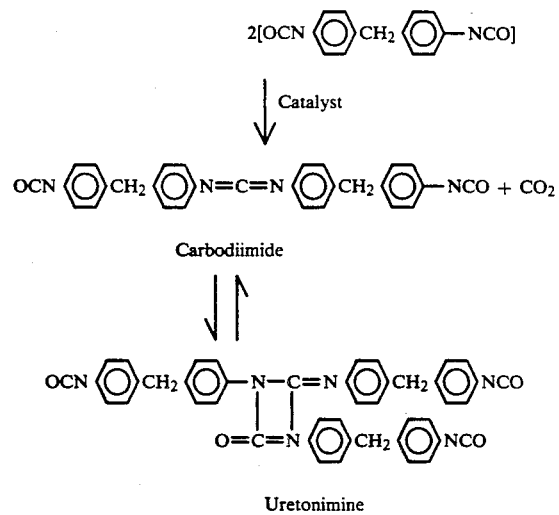

Examples of commercial materials of this type are Dow's ISONATE ® 125M (pure MDI) and ISONATE ® 143L ("liquid" MDI). Preferably, the amount of isocyanates used is the stoichiometric amount based on all the ingredients in the formulation or greater than the stoichiometric amount.

Of course, the term "isocyanate" also includes quasi-prepolymers of isocyanates or polyisocyanates with active hydrogen containing materials. The active hydrogen containing materials can include, but are not limited to, a polyol or polyols, a high molecular weight polyoxyalkyleneamine or combinations thereof.

The polyols include polyether polyols, polyester diols, triols, tetrols, etc., having an equivalent weight of at least about 500, and preferably at least about 1,000 up to about 3,000. Those polyether polyols based on trihydric initiators of about 4,000 molecular weight and above are especially preferred. The polyethers may be prepared from ethylene oxide, propylene oxide, butylene oxide or mixtures of propylene oxide, butylene oxide and/or ethylene oxide. Other high molecular weight polyols which may be useful in this invention are polyesters of hydroxyl terminated rubbers, e.g., hydroxyl terminated polybutadiene. Hydroxyl terminated quasi-prepolymers of polyols and isocyanates are also useful in this invention.

Especially preferred are amine terminated polyether polyols, including primary and secondary amine terminated polyether polyols of greater than 1,500 average molecular weight having from about 2 to about 6 functionality, preferably from about 2 to about 3, and an amine equivalent weight of from about 750 to about 4,000. Mixtures of amine terminated polyethers may be used. In a preferred embodiment, the amine terminated polyethers have an average molecular weight of at least about 2,000. These materials may be made by various methods known in the art.

The amine terminated polyether resins useful in this invention, for example, are polyether resins made from an appropriate initiator to which lower alkylene oxides, such as ethylene oxide, propylene oxide, butylene oxide or mixtures thereof are added with the resulting hydroxyl terminated polyol then being aminated.

When two or more oxides are used, they may be present as random mixtures or as blocks of one or the other polyether. In the amination step, it is highly desirable that the terminal hydroxyl groups in the polyol be essentially all secondary hydroxyl groups for ease of amination. Normally, the amination step does not completely replace all of the hydroxyl groups. However, the majority of hydroxyl groups are replaced by amine groups. Therefore, in a preferred embodiment, the amine terminated polyether resins useful in this invention have greater than 50 percent of their active hydrogens in the form of amine hydrogens. If ethylene oxide is used, it is desirable to cap the hydroxyl terminated polyol with a small amount of higher alkylene oxide to ensure that the terminal hydroxyl groups are essentially all secondary hydroxyl groups. The polyols so prepared are then reductively aminated by known techniques, for example, as described in U.S. Pat. No. 3,654,370, the contents of which are incorporated herein by reference.

In the practice of this invention, a single high molecular weight amine terminated polyol may be used. Also, mixtures of high molecular weight amine terminated polyols, such as mixtures of di- and trifunctional materials and/or different molecular weight or different chemical composition materials, may be used.

Also, high molecular weight amine terminated polyethers or simply polyether amines are included within the scope of our invention and may be used alone or in combination with the polyols described above. The term "high molecular weight" is intended to include polyether amines having a molecular weight of at least about 2,000. Particularly preferred are the JEFFAMINE ® series of polyether amines available from Texaco Chemical Company; they include JEFFAMINE D-2000, JEFFAMINE D-4000, JEFFAMINE T-3000 and JEFFAMINE T-5000. These polyether amines are described with particularity in Texaco Chemical Company's product brochure entitled, THE JEFFAMINE POLYOXYALKYLENEAMINES.

The (B) component of the present polyurea elastomer system includes an amine terminated polyoxyalkylene polyol and a chain extender. The amine terminated polyoxyalkylene polyol is preferably selected from diols or triols and, most preferably, includes a blend of diols and/or triols. The particular polyols, i.e., diols and/or triols, employed in component (B) are the same as those described hereinabove in connection with the quasi-prepolymer of component (A).

The chain extenders used to prepare the polyurea elastomers of this invention are generally described as piperazine derivatives which are used in combination with DETDA. The piperazine derivative component of the chain extenders are prepared, for instance, by reacting, in one step, a 2-amino-2-alkyl-1-alkanol in the presence of a catalyst. More specifically, the alkyl is selected from a $C_1$ to $C_4$ alkyl and the alkanol is a $C_3$ to $C_6$ alkanol which, in turn, results in the co-production of tetraalkylpiperazines and tetraalkylpiperazinones. Most preferably, the alkyl employed is methyl and the alkanol is propanol. Thus, the most preferred piperazine derivatives are 2,2,5,5-tetramethylpiperazine and 3,3,6,6-tetramethylpiperazinone which are the products co-produced by reacting 2-amino-2-methyl-1-propanol in the presence of the catalyst described below. The alkyl group of the tetraalkylpiperazines and tetraalkylpiperazinones can, in addition to methyl, be a $C_2$-$C_4$ alkyl.

The catalyst used to prepare the tetraalkylpiperazine component of the chain extenders described above comprises nickel in combination with one or more other transition metals. Most preferably, the catalyst used to prepare the piperazine derivative component of the chain extender is a nickel-iron-copper-manganese catalyst which, in a preferred embodiment, includes from about 20 to about 40 weight percent nickel, from about 15 to about 30 weight percent iron, from about 20 to about 40 weight percent copper, and from about 2 to about 15 weight percent manganese.

The catalyst used to produce the piperazine derivative component of the present chain extenders are prepared, in a preferred embodiment, by adding a solution of nickel, iron, copper and manganese nitrates, and a solution of sodium carbonate simultaneously to a reaction flask. The pH should be maintained at a level of about 7 by controlling the flow rate of the respective solutions in a manner known by those skilled in the art. The resulting precipitated carbonates should be washed, filtered and subsequently dried at a temperature of about 100° C. to about 150° C. for about 5 to about 20 hours. The dry carbonates are then decomposed at about 350° C. to about 500° C. for about 4 hours to about 8 hours to the corresponding oxides. The oxides are then reduced with hydrogen at a temperature of about 350° C. The reduced catalyst is then stabilized by air. The reduced catalyst can then be added into 3% of graphite and then tableted.

The reaction described above typically takes place at a temperature of about 190° C. to about 260° C. and a pressure of about 100 psig to about 3500 psig.

The chain extenders of the present invention include a combination of the tetraalkylpiperazine described above and 1-methyl-3,5-diethyl-2,4-diaminobenzene or 1-methyl-3,5-diethyl-2,6-diaminobenzene (both of these materials are also called diethyltoluenediamine or DETDA). The chain extender includes from about 1 to about 30 weight percent of the piperazine derivative and from about 99 to about 70 weight percent of DETDA.

Referring once again to the polyurea elastomer of the present invention, the (A) and (B) components react to form the present elastomer system without the aid of a catalyst. However, if desired, a catalyst can be used.

Catalysts, such as tertiary amines or an organic tin compound, may suitably be a stannous or stannic compound, such as a stannous salt of a carboxylic acid, a trialkyltin oxide, a dialkyltin dihalide, a dialkyltin oxide, etc., wherein the organic groups of the organic portion of the tin compound are hydrocarbon groups containing from 1 to 8 carbon atoms. For example, dibutyltin dilaurate, dibutyltin diacetate, diethyltin diacetate, dihexyltin diacetate, di-2-ethylhexyltin oxide, dioctyltin dioxide, stannous octoate, stannous oleate, etc., or a mixture thereof, may be used.

Tertiary amine catalysts include trialkylamines (e.g., trimethylamine, triethylamine); heterocyclic amines, such as N-alkylmorpholines (e.g., N-methylmorpholine, N-ethylmorpholine, dimethyldiaminodiethylether, etc.), 1,4-dimethylpiperazine, triethylenediamine, etc.; and aliphatic polyamines, such as N,N,N'N'tetramethyl-1,3-butanediamine.

Other conventional formulation ingredients may be employed in component (A) or (B) as needed, such as, for example, foam stabilizers, also known as silicone oils or emulsifiers. The foam stabilizers may be an organic silane or siloxane. For example, compounds may be used having the formula:

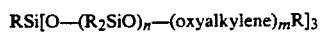

wherein R is an alkyl group containing from 1 to 4 carbon atoms; n is an integer of from 4 to 8; m is an integer of from 20 to 40; and the oxyalkylene groups are derived from propylene oxide and ethylene oxide. See, for example, U.S. Pat. No. 3,194,773.

Pigments, for example, titanium dioxide, may be incorporated in the elastomer system, preferably in the (B) component, to impart color properties to the elastomer.

Post curing of the elastomer of the invention is optional. Post curing will improve some elastomeric properties, such as heat sag. Employment of post curing depends on the desired properties of the end product.

The (A) component and (B) component of the present polyurea elastomer system are combined or mixed under high pressure; most preferably, they are impingement mixed directly in the high pressure equipment, which is, for example, a GUSMER ®H-V proportioner fitted with a GUSMER Model GX-7 spray gun where open mold work or coating is desired or, where closed mold work is desired (e.g., RIM or RRIM), the proportioner can be fitted with standard RIM or RRIM equipment. In particular, a first and second pressurized stream of components (A) and (B), respectively, are delivered from two separate chambers of the proportioner and are impacted or impinged upon each other at high velocity to effectuate an intimate mixing of the two components and, thus, the formation of the elastomer system, which is then delivered onto or into the desired substrate via the spray gun or RIM equipment. If desired, the present polyurea elastomer can be used for pour gun work, such as electrical potting work, and when used in this capacity, the high pressure equipment can be fitted, for example, with a GUSMER ARC pour gun.

The volumetric ratio of the (A) component to the (B) component is generally from about 30 to 70 percent to about 70 to 30 percent.

| GLOSSARY OF TERMS AND MATERIALS | |
|---|---|
| ISONATE ® 143L | Carbodiimide modified liquid MDI; a product of the Dow Chemical Company. |
| THANOL ® SF-5505 | A 5500 molecular weight polyether triol containing approximately 80% primary hydroxide groups; a product of ARCO Chemical Company. |
| JEFFAMINE ® D-2000 | Polypropylene oxide diamine of about 2000 molecular weight; a product of Texaco Chemical Company. |
| JEFFAMINE ® D-4000 | Polypropylene oxide diamine of about 4000 molecular weight; a product of Texaco Chemical Company. |
| JEFFAMINE ® T-5000 | Polypropylene oxide triamine of about 5000 molecular weight; a product of Texaco Chemical Company. |

The following examples are provided to further illustrate preferred embodiments of the present invention and should not be construed as limiting the present invention in any way.

In Examples I and II, certain specific piperazine derivatives are provided. In (comparative) Example III, an attempt was made to synthesize the products of Examples I and II. In Examples IV and V, polyurea elastomers of the present invention are prepared. Also, in Examples IV and V, all spray work was performed with a GUSMER H-V high pressure proportioner fitted with a GUSMER Model GX-7 spray gun. The elastomer systems were sprayed using a block temperature of 160° F. on the (A) component side and 150° F. on the (B) component side, with a hose temperature of 160° F. The system output was 20 lbs/min with a line pressure ranging from 2600 to 2800 psig on the (A) component side and from 2000 to 2200 psig on the (B) component side. Each of the elastomer systems produced in the examples were mixed at an (A):(B) volumetric ratio of 1:1.

EXAMPLE I

In this example, 139 cc of a Ni-Fe-Cu-Mn catalyst (⅛" diameter) were charged to an 0.815" ID tubular upward flow reactor. A liquid feed containing 2-amino-2-methyl-1-propanol and tetraglyme (a tetraethylene glycol dimethyl ether solvent) (1/1.18 by weight) was pumped through the catalyst bed at a rate of 0.12 lb/hr at 240° C. Hydrogen was also passed through the reactor at a rate of about 6 L/hr. The pressure was maintained at 800 psig. The products were collected. GLC analysis showed that a 62% yield of 2,2,5,5-tetramethylpiperazine and a 14% yield of 3,3,6,6-tetramethyl-2-piperazinone were obtained with a 90% conversion of 2-amino-2-methyl-1-propanol. The resulting reaction mixture was fractionally distilled at atmospheric pressure under nitrogen. Both products were further recrystallized from ether.

EXAMPLE II

An additional sample of 2,2,5,5-tetramethylpiperazine and 3,3,6,6-tetramethylpiperazinone was prepared by substantially following the procedure set forth in Example I. In this example, however, the liquid feed contained diglyme (0.94/1 by weight) and the reaction temperature was 235° C. GLC analysis showed that a 58% yield of 2,2,5,5-tetramethylpiperazine and a 14% yield of 3,3,6,6-tetramethyl-2-piperazinone were obtained with an 85% conversion of 2-amino-2-methyl-1-propanol.

EXAMPLE III

In this non-inventive example, an attempt was made to synthesize the compounds produced in Examples I and II. The procedure of Example I was substantially followed, except that, in this example, the catalyst employed was a Ni-Cu-Cr catalyst and the pressure was maintained at 400 psig. GLC analysis showed the presence of many compounds indicating poor selectivity, with that of 2,2,5,5-tetramethylpiperazine being less than 30%.

EXAMPLE IV

The (A) component of a polyurea elastomer was prepared by combining 60 parts of ISONATE 143L and 40 parts of THANOL SF-5505 to form a quasi-prepolymer. The (B) component was prepared by combining 13.27 parts of JEFFAMINE T-5000, 36.5 parts of JEFFAMINE D-4000, 16.59 parts of JEFFAMINE D-2000, and 33.64 parts of DETDA. The (A) and (B) components were mixed in the high pressure equipment, which was fitted with a spray gun. The resulting elastomer was prayed onto a flat metal substrate coated with a zinc stearate based external mold release agent. The gel time was 1.8 seconds.

EXAMPLE V

The (A) component of the polyurea elastomer produced in this example was prepared in accordance with Example IV. The (B) component was prepared by combining 13.42 parts of JEFFAMINE T-5000, 36.91 parts of JEFFAMINE D-4000, 16.78 parts of JEFFAMINE D-2000, 30.20 parts of DETDA and 2.69 parts of 2,2,5,5-tetramethylpiperazine. The resulting elastomer was mixed and sprayed in accordance with Example IV. The gel time was 1.5 seconds.

The physical properties of the polyurea elastomers prepared in Examples IV and V were determined; the results are reported in Table 1.

TABLE 1

| Physical Properties | Example IV | Example V |
|---|---|---|
| Tensile (psi) | 1771 | 1996 |
| Elongation (%) | 66.7 | 120 |
| Tear (pli) | 429 | 427 |
| Shore D Hardness | | |
| (0 sec) | 52 | 52 |
| (10 sec) | 47 | 46 |
| Flexural Modulus (psi) | | |
| (77° F.) | 36369 | 41121 |
| (158° F.) | 28498 | 25313 |
| (−20° F.) | 66497 | 80627 |
| Heat Sag | | |
| (100 mm - 250° F./60 min) | 1.0 | 0 |
| (150 mm - 250° F./60 min) | 3.6 | 4.3 |

As these data demonstrate, the polyurea elastomer system incorporating the chain extenders of this invention process similarly to those polyurea elastomer systems which incorporate DETDA as the chain extender. Furthermore, the polyurea elastomer of the present invention exhibits an improved cure rate and tensile strength.

What is claimed is:

1. A polyurea elastomer comprising an (A) component which includes an isocyanate and a (B) component which includes (1) an amine terminated polyoxyalkylene polyol and (2) a chain extender which includes a minor amount of a tetraalkylpiperazine and a major amount of diethyltoluenediamine.

2. The elastomer of claim 1 wherein said isocyanate of component (A) comprises a quasi-prepolymer of said isocyanate and a material selected from at least one polyol, a high molecular weight polyoxyalkyleneamine or a combination of said materials.

3. The elastomer of claim 2 wherein said at least one polyol of said quasi-prepolymer and said amine terminated polyoxyalkylene polyol of component (B) comprise polyether polyols or polyester polyols having an equivalent weight of at least about 500.

4. The elastomer of claim 3 wherein said polyester polyols are polyesters of hydroxyl terminated rubbers.

5. The elastomer of claim 3 wherein said polyether polyols are selected from the group consisting of polyols based on trihydric initiators having a molecular weight of at least about 4000; amine terminated polyether polyols having an average molecular weight greater than 1500, a functionality of from about 2 to about 6 and an amine equivalent weight of from about 750 to about 4000; and mixtures thereof.

6. The elastomer of claim 5 wherein the functionality of said polyether polyols is from about 2 to about 3.

7. The elastomer of claim 3 wherein said polyether polyols are derived from amine terminated polyether resins having greater than 50 percent of their active hydrogens in the form of amine hydrogens.

8. The elastomer of claim 3 wherein said amine terminated polyoxyalkylene polyol of component (B) is selected from diols, triols or blends thereof.

9. The elastomer of claim 1 wherein said chain extender comprises from about 1 to about 30 weight percent of said tetraalkylpiperazine and from about 99 to about 70 weight percent of diethyltoluenediamine.

10. The elastomer of claim 1 wherein the alkyl group of said tetraalkylpiperazine includes a $C_1$ to $C_4$ alkyl.

11. The elastomer of claim 1 wherein said tetraalkylpiperazine is tetramethylpiperazine.

12. The elastomer of claim 1 wherein the volumetric ratio of the (A) component to the (B) component is from about 30 to about 70 percent of the (A) component to about 70 to about 30 percent of the (B) component.

13. A polyurea elastomer comprising an (A) component which includes a quasi-prepolymer of an isocyanate and a material selected from at least one polyol, a high molecular weight polyoxyalkyleneamine or a combination of said materials; and a (B) component which includes (1) an amine terminated polyoxyalkylene polyol and (2) a chain extender including from about 1 to about 30 weight percent of tetraalkylpiperazine and from about 99 to about 70 weight percent of diethyltoluenediamine, wherein the alkyl group of said tetraalkylpiperazine includes a $C_1$ to $C_4$ alkyl.

14. The elastomer of claim 13 wherein said at least one polyol of said quasi-prepolymer and said amine terminated polyoxyalkylene polyol of component (B) comprise polyether polyols or polyester polyols having an equivalent weight of at least about 500.

15. The elastomer of claim 14 wherein said polyester polyols are polyesters of hydroxyl terminated rubbers.

16. The elastomer of claim 14 wherein said polyether polyols are selected from the group consisting of polyols based on trihydric initiators having a molecular weight of at least about 4000; amine terminated polyether polyols having an average molecular weight greater than 1500, a functionality of from about 2 to about 6 and an amine equivalent weight of from about 750 to about 4000; and mixtures thereof.

17. The elastomer of claim 16 wherein the functionality of said polyether polyols is from about 2 to about 3.

18. The elastomer of claim 14 wherein said polyether polyols are derived from amine terminated polyether resins having greater than 50 percent of their active hydrogens in the form of amine hydrogens.

19. The elastomer of claim 14 wherein said amine terminated polyoxyalkylene polyol of component (B) is selected from diols, triols or blends thereof.

20. The polyurea elastomer of claim 13 wherein said tetraalkylpiperazine is tetramethylpiperazine.

21. A method of making tetraalkylpiperazines and tetraalkylpiperazinones which comprises reacting, in one step, and under suitable reaction conditions, a 2-amino-2-alkyl-1-alkanol in the presence of a catalyst composition which includes nickel and at least one other transition metal.

22. The method of claim 21 wherein said at least one other transition metal includes iron, copper and manganese.

23. The method of claim 22 wherein said catalyst composition further includes from about 20 to about 40 weight percent nickel, from about 15 to about 30 weight percent iron, from about 20 to about 40 weight percent copper and from about 2 to about 15 weight percent manganese.

24. The method of claim 21 wherein said suitable reaction conditions include a temperature of about 190° C. to about 260° C. and a pressure of about 100 psig to about 3500 psig.

25. The method of claim 21 wherein said alkyl of said 2-amino-2-alkyl-1-alkanol includes a $C_1$ to $C_4$ alkyl and said alkanol is a $C_3$ to $C_6$ alkanol.

26. The method of claim 21 wherein the alkyl groups of said tetraalkylpiperazine and said tetraalkylpiperazinone are $C_1$ to $C_4$ alkyls.

* * * * *